May 9, 1950 A. F. DEN BOER Plant Pat. 939
FLOWERING CRAB APPLE TREE
Filed Aug. 30, 1948
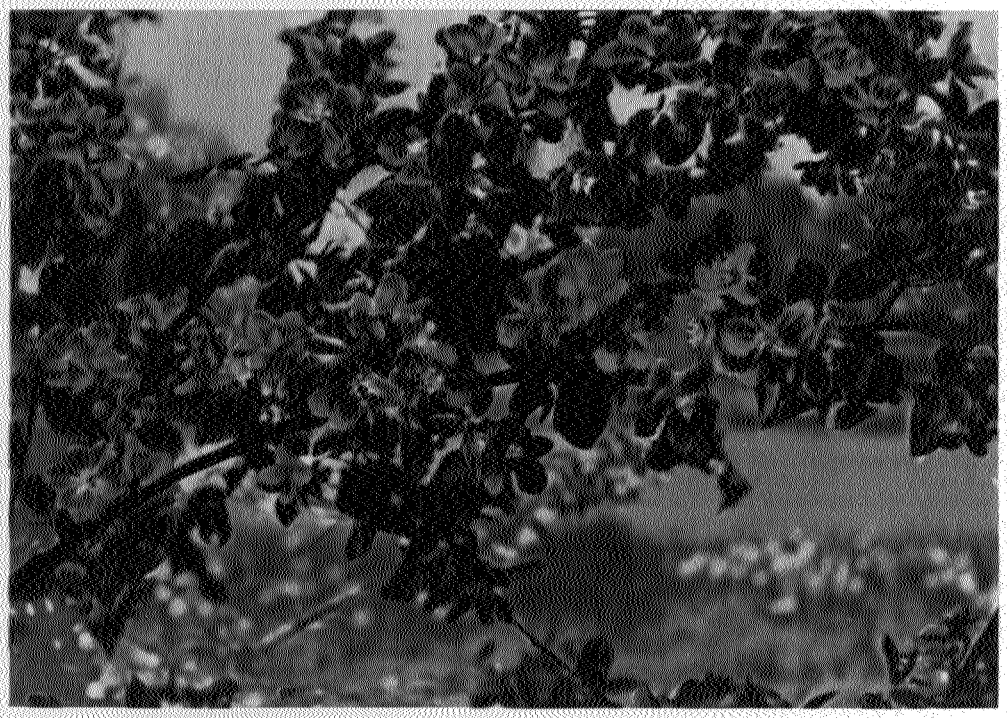
Inventor
Arie F. den Boer
By Robert Robb
Attorney Patented May 9, 1950 Plant Pat. 939

UNITED STATES PATENT OFFICE

939

FLOWERING CRAB APPLE TREE

Arie F. den Boer, Des Moines, Iowa, assignor to John J. Grullemans, Mentor, Ohio Application August 30, 1948, Serial No. 46,745

1 Claim. (Cl. 47—59)

The present invention or discovery relates to a new and distinct variety of ornamental crab apple tree, originating as an open pollenated seedling of Malus "Jay Darling."

The seedling was originally selected because of its extremely dark colored foliage, which is darker than any other horticultural variety with purple colored leaves. This dark foliage is combined with other outstanding features of novelty, such as:

(1) The unique color of the open blossoms which differs from other so-called red or purplish red flowered varieties in that it is a brighter red and contains less purple or magenta tones.

(2) The rather slow growth of the plant which makes it exceptionally desirable for gardens of limited dimensions.

(3) Its extreme hardiness, so essential in a plant where its utility resides primarily in its floriferousness in a season subject to occasional low seasonal temperatures.

This new hybrid variety differs from its seed parent in that it is smaller in stature and of slower growth, and its flowers are more red and are in part, semi-double. Also, as before premised, the foliage is darker in color and retains that color much longer; the fruit is smaller and somewhat darker in color.

This combination of semi-double blossom and dark foliage distinguish this new variety from other known purple-leaved and purple-flowered hybrids and none of the other flowering crab apples known as "Rosybloom" crabs, originated in Canada, have blossoms and foliage which resemble in any way the blossoms or foliage of the present variety herein disclosed. This statement is based on the extensive study made by me of approximately 300 kinds or types of the "Rosybloom" series, both of the commercial and the ornamental classes, grown in Des Moines, Iowa, and the actual growing of many of the ornamental crabs of this series by myself. There is not a single one which is not distinct from the present new variety. Not one has the bright red flowers of the new variety, nor do any of them have the semi-double blossoms. Although several have purplish foliage at the start of the season, this new hybrid has much darker foliage then and through the growing season grows still much darker in color than the "Rosyblooms." So distinct is this new variety, that even amateurs, without training, are able to distinguish it from all others. Even though the "Sissipuk" variety of this series is one of more or less dwarfish habit, it is altogether a different looking plant.

"Sissipuk" is also one of the darkest reds of the "Rosyblooms," but it nevertheless does not have the clear red with only the remotest trace of purple that is characteristic of this new variety. The parent variety "Jay Darling" crab is a much larger tree with single flowers of a less bright tint, so that this new variety differs from any of the known "Rosybloom" series.

The characteristics above referred to come true to form in the progeny of this variety and are established.

In the accompanying drawing are illustrated specimens of the flowers and foliage as nearly as these can be depicted by hand artistry.

The following is a specific description of the new variety, color terminology being in accordance with Ridgway's Color Standards and Nomenclature, except where otherwise indicated to have ordinary dictionary significance:

*Tree*

Habit of growth: Upright; spreading.

Blooming habit: Early, about May 1st to 10th in the location of Des Moines, Iowa, lasting from eight to ten days.

Hardiness: Extremely hardy.

Branches:

*Twigs.*—Color—Hay's Maroon, Plate XIII, to Dull Purplish Black, Plate L.

*Lenticels.*—Small. Color—Pale Quaker Drab, Plate LI, to Heliotrope Gray, Plate L.

*Older branches.*—Color — Analine Black, Plate L, with Pale Mouse Gray bloom, Plate LI.

*Trunk.*—Scaly. Color—Deep Mouse Gray, to Iron Gray, Plate LI.

Leaves:

*Color.*—First Hay's Maroon, Plate XIII, later Carob Brown, Plate XIV. Foliage retains the Carob Brown color until fall. Also, in the leaves, Cedar Green, Plate VI, with Carob Brown diffusion on edges and on some ribs.

Flowers:

*Size.*—1½–1¾ inches across.

*Buds.*—Closed—Deep purplish red, Pomegranate Purple, Plate XII. Half open—Deep purplish red (Pomegranate Purple, Plate XII) to Deep Rose Red, Plate XII. Fully expanded—Deep Rose Red, Plate XII, to bright Rose Color, Plate XII, with trace of Tyrian Rose, Plate XII; claw and base of petals white or nearly white to Rood's Lavender, Plate XLIX; veins of the claw and in the light tinted base of the petal are Deep Vivid Purple, Plate XXXVII.

*Number of petals.*—Usually five, but about 10% of the blossoms have from six to nine petals.

*Stamens.*—Usually 20, occasionally 18 or 19; occasionally 1 or 2 petaloids.

*Anthers.*—Color—first purplish, Dull Magenta Purple, Plate XXVI, opening to Cream-Buff, to Chamois, Plate XXV. Stand out well above the flower.

*Filaments.*—Pansy Purple, Tyrian Rose, Plate XII, at the base; long.

*Styles.*—Slightly longer than stamens; Rood's Lavender; five, rarely less, hairy only at extreme base.

*Pedicel.*—Pansy Purple, Plate XII, slender; slightly pubescent; 1"–1⅛" long.

*Calyx.*—Blackish Red Purple, Plate XII; pubescent.

*Sepals.*—Blackish Red Purple, Plate XII; slight pubescent inside and out.

Fruit: Globose; about ⅝" across. Color—Blackish Red Purple, Plate XII.

I claim:

A new and distinct variety of ornamental flowering crab apple tree characterized as to novelty by its habit of slow growth, extreme hardiness, the color of its open blossoms, in part semi-double, and the very dark coloring of its foliage, substantially as shown and described.

ARIE F. DEN BOER.

No references cited.